United States Patent
Szalay et al.

(10) Patent No.: US 10,592,617 B2
(45) Date of Patent: Mar. 17, 2020

(54) COMPUTER IMPLEMENTED METHOD, PROCESSOR DEVICE AND COMPUTER PROGRAM PRODUCT FOR DESIGNING INTERVENTION INTO REAL COMPLEX SYSTEMS

(71) Applicant: TURBINE SIMULATED CELL TECHNOLOGIES LIMITED, London (GB)

(72) Inventors: Kristóf Zsolt Szalay, Budapest (HU); Péter Csermely, Budapest (HU)

(73) Assignee: TURBINE SIMULATED CELL TECHNOLOGIES LIMITED, London (GB)

( * ) Notice: Subject to any disclaimer, the term of this patent is extended or adjusted under 35 U.S.C. 154(b) by 295 days.

(21) Appl. No.: 15/105,749

(22) PCT Filed: Dec. 17, 2014

(86) PCT No.: PCT/HU2014/000126
§ 371 (c)(1),
(2) Date: Jun. 17, 2016

(87) PCT Pub. No.: WO2015/092454
PCT Pub. Date: Jun. 25, 2015

(65) Prior Publication Data
US 2016/0350461 A1   Dec. 1, 2016

(30) Foreign Application Priority Data
Dec. 18, 2013   (HU) .................................... 1300737

(51) Int. Cl.
*G01N 33/48* (2006.01)
*G01N 33/50* (2006.01)
(Continued)

(52) U.S. Cl.
CPC .......... *G06F 17/5009* (2013.01); *G06F 17/18* (2013.01); *G06F 17/509* (2013.01);
(Continued)

(58) Field of Classification Search
None
See application file for complete search history.

(56) References Cited

U.S. PATENT DOCUMENTS

2009/0204374 A1   8/2009   Hill et al.
2011/0153302 A1   6/2011   Mitsos et al.
(Continued)

FOREIGN PATENT DOCUMENTS

EP   2 530 615 A1   12/2012
WO   2005/111905 A2   11/2005

OTHER PUBLICATIONS

Gardner et al. Parallel genomic sequence-searching on an ad-hoc grid: Experiences, lessons learned, and implications. Proceeding of the 2006 IEEE/ACM Conference, 14 pages. (Year: 2006).*

*Primary Examiner* — Russell S Negin
(74) *Attorney, Agent, or Firm* — Laura L. Hupp; Merchant & Gould P.C.

(57) ABSTRACT

A computer-implemented method for designing intervention into the behavior of a real complex system of technical or biochemical nature. The real complex system is modeled by a network of objects and relations between the objects. The objects of the system are represented by network points and the relations are represented by edges between the network points. The states of the objects are described by a parameter set and the relations associated with the edges are described by functions of time.

17 Claims, 4 Drawing Sheets

Figure 1:
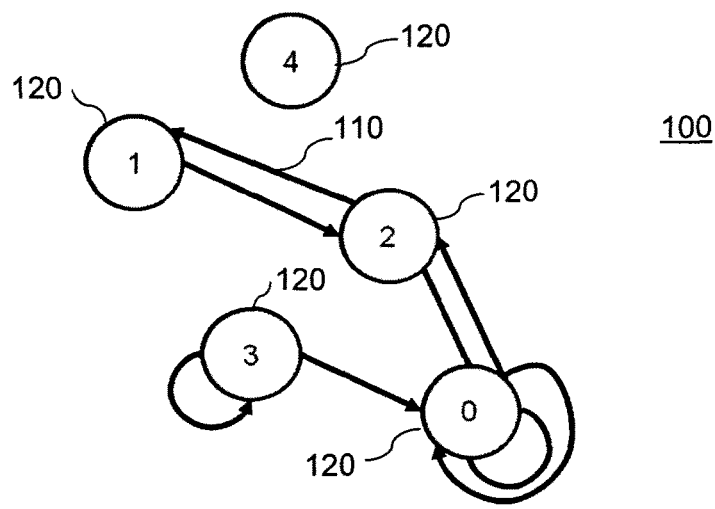

(51) Int. Cl.
*G06F 17/50* (2006.01)
*G06N 7/00* (2006.01)
*G16B 5/00* (2019.01)
*G06N 20/20* (2019.01)
*G06N 5/00* (2006.01)
*G06F 17/18* (2006.01)
*G06N 3/12* (2006.01)

(52) U.S. Cl.
CPC ............ *G06N 3/126* (2013.01); *G06N 5/003* (2013.01); *G06N 7/005* (2013.01); *G06N 20/20* (2019.01); *G16B 5/00* (2019.02)

(56) References Cited

U.S. PATENT DOCUMENTS

2011/0264420 A1   10/2011  Sander et al.
2013/0297276 A1*  11/2013  Imai .................... G16C 99/00
                                                          703/12

* cited by examiner

COMPUTER IMPLEMENTED METHOD, PROCESSOR DEVICE AND COMPUTER PROGRAM PRODUCT FOR DESIGNING INTERVENTION INTO REAL COMPLEX SYSTEMS

This is the national stage of International Application PCT/HU2014/000126, filed Dec. 17, 2014.

In general, the present invention relates to modeling and simulation of real complex systems. More particularly, the present invention relates to a computer-implemented method, a processor device and a computer program product for designing intervention into real complex systems, wherein the complex system is of technical or biochemical nature and modeled by a network in which objects of the system are represented by points and the relations between the objects are represented by edges between the network points, and wherein the state of the objects are described by a set of parameters and the relations associated with the edges are described by functions of time.

In the recent decades, the network approach became a wide-spread method of studying complex systems. For example, protein structure networks, in which the network points represent proteins and the network edges represent the distances between them, are used to describe the changes in the development of protein complexes and in their structure, as well as to describe binding of agents or the effects of enzymes, to an increasingly larger extent. In the recent years, a number of computer program systems have been introduced that are capable of building protein structure networks based on 3D structural data, as well as analyzing the networks that have been built up. The networks describing the interactions between the proteins (interactomes) help a lot in understanding the molecular level mechanism of the cellular functions and the development of diseases, and in designing medicines. Nowadays, research into network dynamics is essential for understanding the behavior of complex systems.

The patent specification US 2009/0204374 deals with modeling interactions of the several genes, proteins and the other components of cell, applying mathematical techniques to represent the relations between the cell components and the manipulation of the dynamics of the cell. The object of the system and the method described in this patent specification is to determine whether one or more components of a cell may be a target for interaction with therapeutic agents in the modeled biological system. The method comprises the steps of identifying those cellular components by simulation that are supposed to be targets of therapeutic agents. During the simulation, perturbations are carried out in the network modeling the biological system by removing one or more elements from the network, by modifying the concentration of one or more elements or the mathematical equations representing the interrelationships between certain elements. After perturbation the next state of the network is determined, and based on the result of the comparison between the subsequent states, those elements are then identified that made an interaction with one or more therapeutic agents.

The drawback of the above method is that perturbation of the network is carried out only in certain network points and on the basis of this perturbation, it is only examined which elements and which effect are made by the particular therapeutic agent. This method does not allow determining through which perturbations a target state can be reached or at least approached from an initial state with a reasonably small error.

It is an object of the present invention to improve the known network analysis methods and to provide a method for designing an intervention in a complex system by using a network adapted for modeling the complex system and carrying out simulations of the network. More particularly, it is an object of the present invention to determine, in the network that models the complex system, an excitation or a set of excitations which transfers the complex system from a predetermined initial state into an also predetermined target state or into a state approximating said target state as much as possible.

It is another object of the present invention to provide a device for carrying out the method of the invention.

The above objects are achieved by providing a computer-implemented method for designing intervention into the behavior of a real complex system of technical or biochemical nature, wherein the real complex system is modeled by a network of objects and relations between said objects, wherein said objects of the system are represented by network points and said relations are represented by edges between the network points, and wherein the states of the objects are described by a parameter set and the relations associated with the edges are described by functions of time, wherein the method comprises the steps of:

a) for each object of the real system, obtaining values for each parameter of said parameter set both for an initial state and a desired target state thereof, b) setting the initial values and the desired target values of the parameters of the network points, c) in a predetermined manner, generating an initial set of test excitations for at least one point of the network, set initial set of text excitations including a predetermined number of test excitations, d) simulating the behavior of the network by using the set of test excitation, e) detecting whether a termination condition in a given simulation step is true and if so, stopping the simulation, f) after stopping the simulation, calculating and storing, for each network point, the difference between the parameter values belonging to the desired target state and the parameter values produced by the simulation, g) based on said differences and said number of the test excitations, generating a next set of test excitations by using a predetermined algorithm, h) repeating steps d)-g) until a predetermined termination condition is satisfied, i) from among the stored simulation results, selecting the simulation result best matching the desired target state, and the test set of excitations, which produced said best matching simulation result, is regarded as a final excitation set transferring the network from its initial state to its target state, and j) outputting the final excitation set.

Preferably, in the method the perturbations are generated using a genetic algorithm, simulated annealing with one or more cycles, or other metaheuristics, but it is also appreciated that the perturbations are generated entirely randomly.

The above objects are further achieved by providing a processor device for designing intervention into the behavior of a real complex system, wherein the real complex system is of technical or biochemical nature and modeled by a network in which the objects of the system are represented by network points and the interrelationships between the objects are represented by edges between the network points, and wherein the states of the objects are described by a parameter set and the relations associated with the edges are described by functions of time. The device comprises a data carrier adapted for storing the network structure, the parameter values of the network points, the functions of interactions associated with the network edges. The data carrier further comprises a computer program for modeling the behavior of the network. The device further comprises a memory unit, a central processing unit electronically coupled to the data carrier and the memory unit. The central processing unit comprises a data input unit, a metaheuristics unit for generating a test set of excitations by using any one of a genetic algorithm, the simulated annealing algorithm and any metaheuristics, a simulation unit for simulating the network, and a comparison unit for comparing the target state or the steady state of the simulation with the target state of the simulation.

Finally, the above objects are achieved by providing a non-transitory computer program product comprising computer readable instructions which, when run on a computer, cause the computer to carry out the steps of the above method.

By using the method according to the present invention, through specifying an initial state and a target state of the network, the parameters of an excitation which transits the network from a given initial state to a given target state by using nearly the minimum number of network points (nodes) can be determined. The resulting parameters of the excitation may be, for example, identifiers of the network points requiring an excitation, or the function, the sign, the volume, the time period, the discontinuity, etc. of the excitations.

Figure 2:
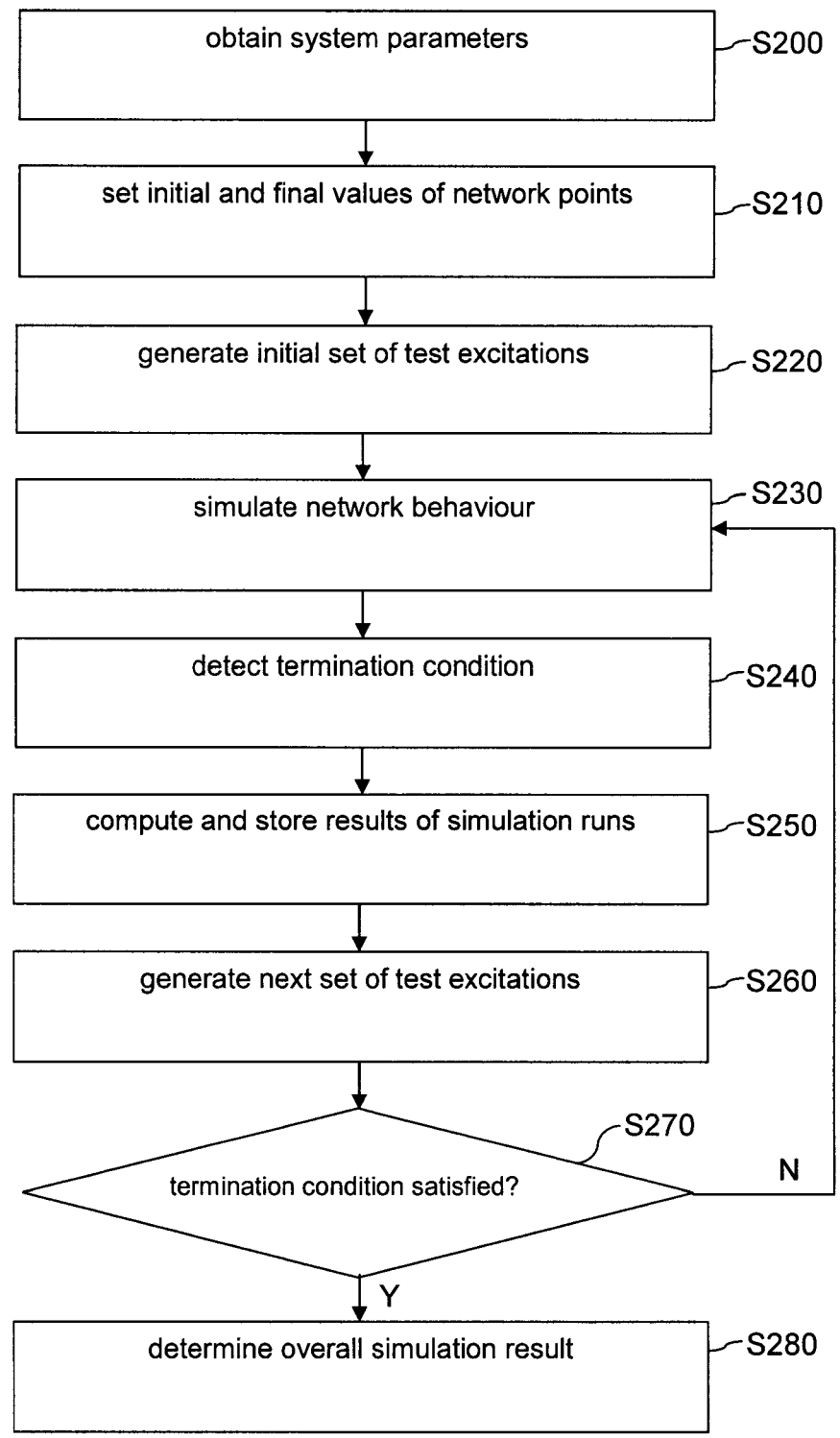
Figure 3:
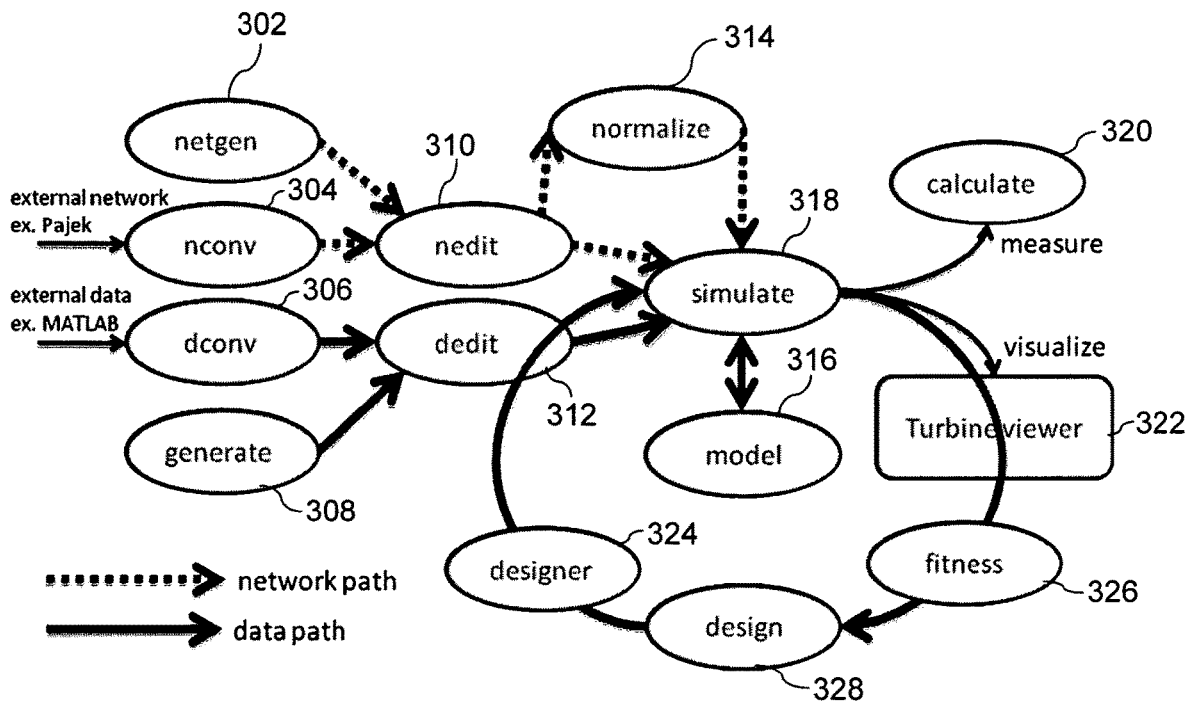
Figure 4:
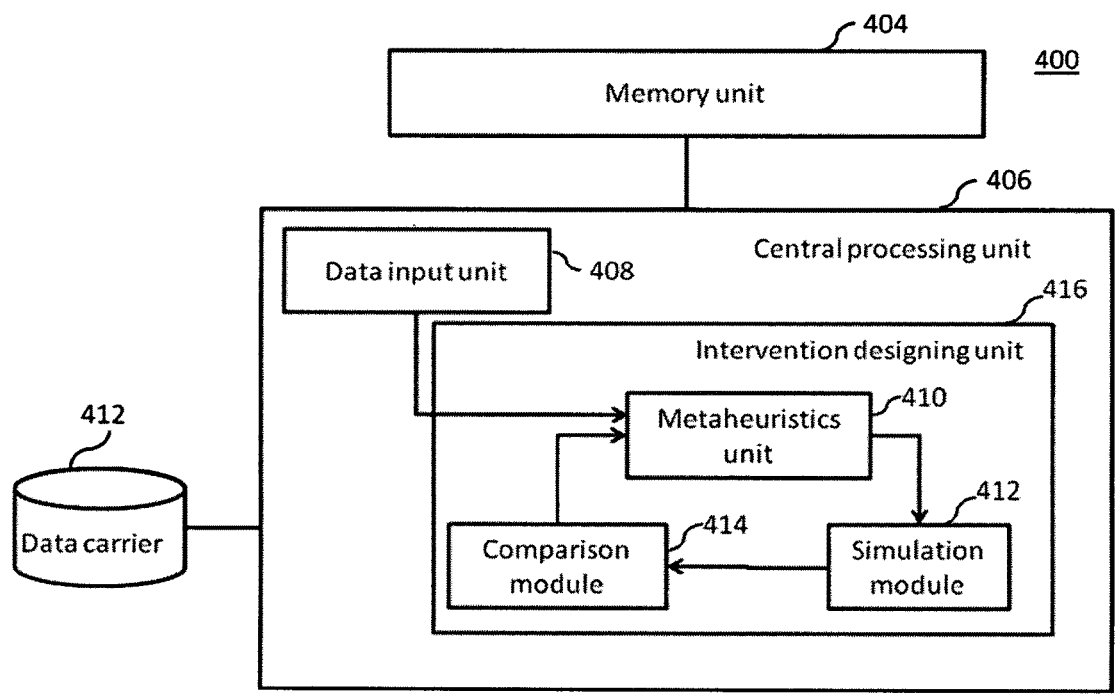
Figure 5:
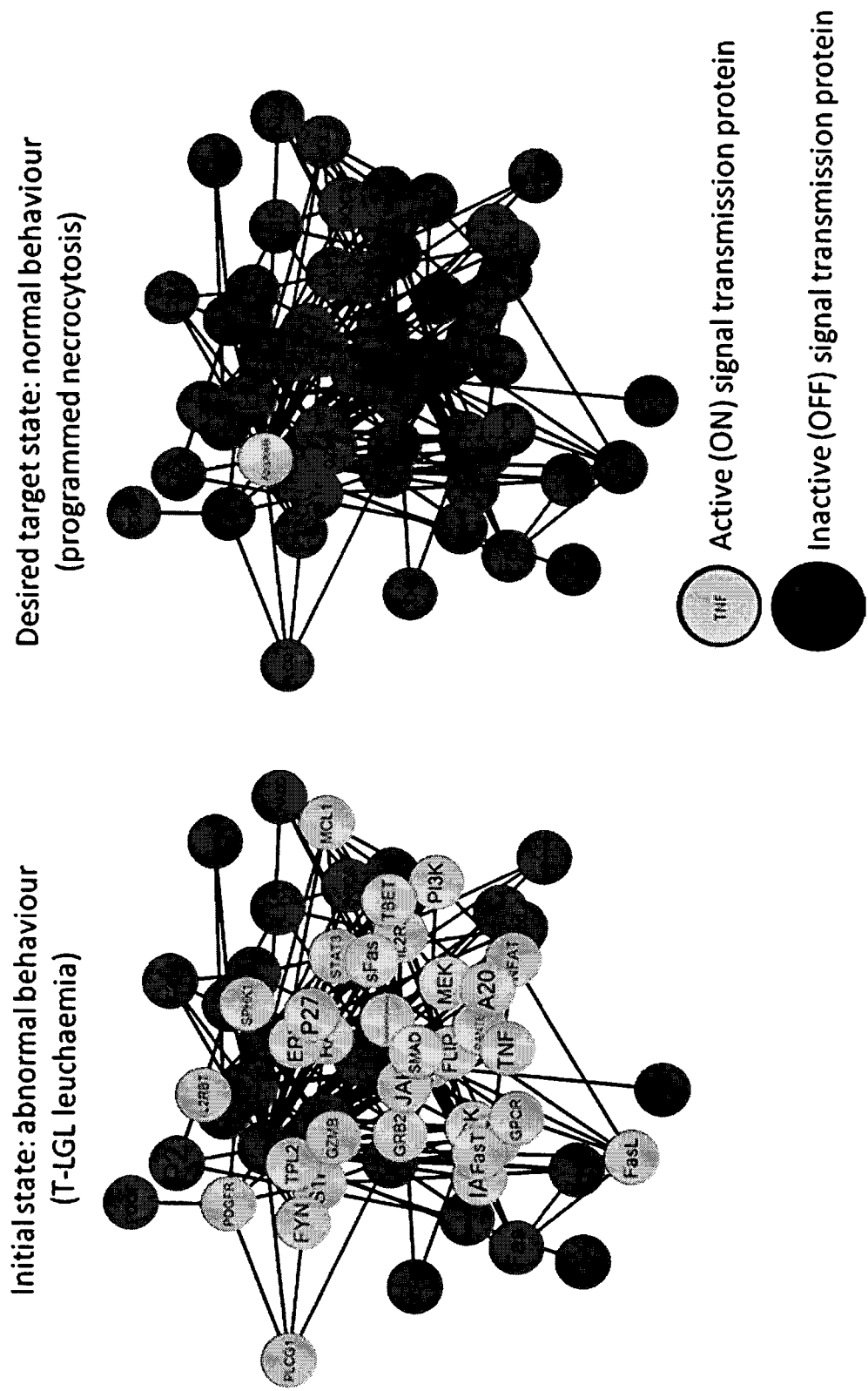

In the following, the invention and some of its preferred embodiments will be described with reference to the drawings, in which FIG. 1 schematically illustrates a network model used in the method according to the invention, FIG. 2 depicts a flow diagram showing the main steps of the method according to the invention, FIG. 3 is a functional block diagram of a system for designing intervention, used for the method according to the invention, FIG. 4 schematically illustrates the main components of a processor device adapted for designing intervention and the connectivity arrangement of said components in accordance with the invention, and FIG. 5 illustrates an example of how the method according to the invention may be applied in the field of molecular biology.

NETWORK STRUCTURE

In FIG. 1, a network model used in the method according to the invention is schematically illustrated. The data structure of the network 100 is a special combination of an adjacency list format known from the literature and an edge list format, wherein a conventional edge list and a half-adjacency list are managed together. For each edge 110 of the network 100 (link structure), the identifiers of the two points 120 located at the ends of the edge, as well as other optional edge parameters are stored. In contrast with a conventional adjacency list, wherein identifiers of the neighbor network points are stored, in the network 100 used in the method according to the invention, the identifiers of all edges 110 connecting to a particular point (node structure) are stored for each network point 120, together with other optional network point parameters. Hence, since only two network points are connected to one edge, the search for the identifiers of the neighbor points during the simulation of the network results in hardly any decrease of speed, while the parameters of the edges connecting to a given point (e.g. edge weight) can be still searched quickly.

The data structure representing a point 120 and the data structure representing an edge 110 both contain an identifier of text type, by means of which a point 120 can be unambiguously identified in the network 100, as well as an identifier of numeric type which is equal to the position of the given network element (point or edge) in the data array describing the network structure. If, for example, the numeric identifier of a point is 12, then it is stored as the 13th element of the "node" structure of the network. Consequently, numbering of the numeric identifiers (indexing) starts from 0 and its maximum value is smaller by one than the number of the edges. Furthermore the numeric identifiers form a continuous sequence, i.e. below the maximum value there is not any identifier that would belong to none of the elements. With each of the points 120 and the edges 110, any kind of numeric parameter (e.g. concentration, temperature, speed, etc. for points; and an edge weight or a transfer function for edges), or even a string parameter (e.g. experimental method by means of which the given edge is obtained) can be associated. It is to be noted that not only a single value but also a vector of arbitrary length may be stored as a numerical parameter, which allows, for example, storing entire transfer functions as edge parameters.

The structure of the network 100 can change during the simulation with the restriction that it is not allowed to delete a point 120 or an edge 110 from the network, otherwise in such a modified network the time functions belonging to the period before the removal of the element becomes uninterpretable. However, removal of a network point or edge may be emulated during the simulation, for example by introducing a state variable "valid", the value of which is different from zero only if the corresponding element was not deleted before that time step. The parameters stored for a network 100 are not allowed to be modified, i.e. no parameter can be deleted and no new parameters can be associated with the network during the simulation (more particularly, during the currently running simulation step). The parameters having a value that may be modified by the simulation are stored as state variables which, in turn, may be stored in data files described below.

Functors

Another basic data structure of the network used in the method according to the invention is a series of functions or a vector of functions (referred to as functor), each row of which contains a function of time, the number of its rows being equal to the element number of the points or the edges. Since we primarily store the time series of the network in the functors, a matrix storage format provides a simple and efficient solution.

The time functions of a functor can be unambiguously associated with the corresponding points or edges of the network. Since the number of the time functions equals to the number of the points or the edges of the network, such a data series can become huge in large networks even at short simulations, therefore it is preferred for the data series to be directly stored on a data carrier without reading them into memory. It is also preferred that during the simulation one can freely select whether a time function is stored in a row-major or a column-major order, which may significantly improve the disc access rate in case of appropriate use.

The functors may contain the number of rows and columns as metadata, that is whether they are stored in a column-major or row-major format, and they may also contain any supplementary text information, such as information on what type of system's operation is described, what kind of presentation is suggested etc.

Each row of a matrix contains the values a state variable of a particular node takes during the simulation. For example, if the simulation has a length of 1000 steps, the 500th column of the 4th row contains the value taken up by the node No. 3 (i.e. fourth node in the series) in the step No. 499 (as the indices of the arrays start at 0).

EXAMPLE 1

| energyN.cdat |
| --- |
| 0 1 2 1 0 |
| 0 0 0 1 2 |
| 3 2 2 1 0 |

The above functor contains the time series of a simulation of 5 steps carried out in a network containing 3 points, wherein in each row belongs to a given point and the subsequent values (i.e. the columns) within the series describe the time-dependent change of the energy of the given point. As it can be seen in the above data file, the initial value of the node No. 3 is 3, while the initial value of the other nodes is 0. In the following steps, the energy of node No. 3 decreases while node No. 1 is being "charged", i.e. its energy increases. In the last step No. 5, the energy of node No. 3 and node No. 1 is depleted, as it is taken over by node No. 2.

The simulated network described by the above functor is thus likely a directed chain in which the initial energy of node No. 3 is transferred to node No. 2 through node No. 1.

Due to the fact that the external excitations (perturbations) are introduced into the simulation by means of the above mentioned data files, the simulation computations become easier since the location and the time of any perturbation can be unambiguously associated with a particular step of the simulation and with a particular node of the network.

EXAMPLE 2

| energyNPF.cdat |
| --- |
| 0 0 0 |
| 0 3 0 |
| 1 2 1 |

The above additive functor results in that the value of the state variable "energy" taken up at node No. 2 is increased by 3 in the second step, and the energy of node No. 3 is increased by 1 in the first step, by 2 in the second step and again by 1 in the third step, independently of its actual value. The energy of node No. 1 has not changed in this case.

By using the above mentioned functors, through generating an appropriate matrix, an excitation (perturbation) with any shape of function may be applied to any one or more network points.

The values of the state variables taken up during the simulation, as well as the triggering parameters and the excitations are preferably stored in separate data files. Since the simulation method applies the corresponding points of the excitation functions directly to the state variables, excitations with any shape and acting on any number of elements may be generated by changing the waveforms of the functions. The data files preferably have two specific settings. Namely, they may be either periodical, wherein the corresponding points of the excitation function are continuously applied until the end of the simulation, or controlled by constraints, wherein the corresponding points of the functions are not added to the actual value of the state variables but they overwrite those values.

Excitation

During the simulation each state of the network is basically characterized by the values of its state variables, i.e. each state is associated with a particular functor, typically in the form of a matrix. In the initial state, the length of the functions of time of a state variable is equal to the rank of that state variable, i.e. it is 1 if the given state variable appears in the system equations only with its actual value; it is 2 if the first derivative thereof also appears; it is 3 if the second derivative thereof also appears, etc.

The excitation functions are preferably defined in a text format, for example in the following way:

EXAMPLE 3

| <ID> <wave form> <parameters> |
| --- |
| 1 dirac 0 1000 |
| 10 gauss 10 3 100 |
| 5 sine 0.1 10 |

In the above definition <ID> is the identifier of the network point on which the excitation is applied, the parameter <wave form> is the name of plug-in the associated time series of which is produced by a corresponding application, and the variable <parameters> includes the parameters required by said plug-in.

In the above example, the parameters of the function "dirac" may be, for example, an offset (the number of the step in which the impulse is to be applied) and an amplitude (the size of the unit impulse), whereas the parameters of the function "gauss" may be, for example, the $\mu$ (the center of the Gaussian curve), the $\rho$ (standard deviation; the width of the curve) and the amplitude, whereas the parameters of the function "sine" may be for example the frequency, the amplitude and the phase.

The excitation specified for the network (e.g. the group of excitations defined in Example 3) may be converted into a matrix form by using an appropriate function which produces the corresponding wave forms in numeric format (as a time series) and fills said plurality of said time series into the respective rows of an empty functor matrix that belong to the corresponding network points. A 11 by 10 functor matrix corresponding to the excitation in text format from the above Example may, for example, be defined in the following way:

EXAMPLE 4

| 0 0 0 0 0 0 0 0 0 0 |
| --- |
| 1000 0 0 0 0 0 0 0 0 0 |
| 0 0 0 0 0 0 0 0 0 0 |
| 0 0 0 0 0 0 0 0 0 0 |
| 0 0 0 0 0 0 0 0 0 0 |
| 0 3 9 9 3 −3 −9 −9 −3 0 |
| 0 0 0 0 0 0 0 0 0 0 |
| 0 0 0 0 0 0 0 0 0 0 |

-continued

```
0 0 0 0 0 0 0 0 0 0
1 2 4 5 10 34 67 88 96 100
```

(Note:
the other half of the Gaussian curve is missing since because of ρ = 3 it would have a length of 20 units, but it is loaded into a functor having a length of only 10 units.)

The number of the excited network points can be adjusted. In case the generation of excitations is controlled by a genetic algorithm, the number of the excited points is adjusted by the genetic algorithm itself. Preferably, one can set a range within which the number of the excited points can vary, and one can also set the values of the excitation parameters. This range-based definition is rather similar to the above format but in this case, intervals are defined. The Example 5 below describes such group of excitations.

EXAMPLE 5

1:10 Dirac 0:10 100:1000

In the above Example, the algorithm may apply an excitation of type Dirac-delta to any one or more or even all of the nodes No. 1-10 with offset values in the range [0 . . . 10] and with an amplitude ranging from 100 to 1000.

Running a Simulation

How the simulation advances along time primarily depends on the network dynamics which, however, physically depend on the properties of the modeled system, meaning that different dynamic equations are to be used for a social network, a biological signal transmission network or in a network modeling the nervous system. The network dynamics are preferably described in a DLL file which can be easily replaced, but even the user itself may create a DLL file which describes dynamics specifically characterizing its own system. From the DLL file a special function PerStep is to be exported which provides the next values of the state variables based on their actual and the previous values.

The increased speed of the method according to the invention results mostly from the data structure of the above described network, which allows a search in the order O(1) for both the edges and the points, i.e. finding the points located at the two ends of an edge or the points adjacent to a given point equally have a time complexity of order O(1).

Since the number of possible excitations during a simulation is uncountably infinite, algorithms controlling conventional searches, such as the algorithm A* cannot be used for controlling the simulations according to the invention, therefore metaheuristics are used. Accordingly, the requested excitation transferring the modeled system from a given initial state to a given target state (or to the proximity thereof) is searched for first by generating one or more test excitations by applying a predetermined method, e.g. randomly or by using a heuristic method, and then by carrying out a simulation on the network, in which simulation said test excitations are used. When the so-called simulated annealing is used in the simulation, one test excitation is generated in every simulation step, whereas in case of applying a genetic algorithm in the simulation, more than one test excitation is generated in every simulation step.

When the network reaches a steady state or a predetermined number of steps has been calculated during the simulation, the differences between the parameters belonging to the actual simulation state and the parameters belonging to the desired target state are calculated, and then a new test set of excitations is generated by using these difference values and the number of the applied excitations, either as energy values (for simulated annealing) or as fitness values (for genetic algorithms), wherein said test set of excitations preferably moves the state of the system somewhat closer to the desired target state. This iterative process is repeated until a predetermined number of iterations is completed or until the fitness value or the energy value decreases below a certain threshold. From among the thus obtained best series of excitations, the excitation with the lowest fitness or energy value is selected and returned as the desired excitation that transfers the system from its initial state to a system state best matching the desired target state. During the simulation it is preferred that within an arbitrarily specified time period, the difference between the simulated state and the desired target state is computed in every simulation moment, and the minimum value thereof is regarded as the final difference, i.e. there is a certain range in which the best matching may be measured. During the simulation, the various test excitations transfer the system into different states, thereby how to find the best excitation is reducible into a graph theory problem. In the field of artificial intelligence, one of the most common issues deals with graph traversal, i.e. how to find the shortest possible way within the shortest possible time between two points of a certain graph like a tree graph. When the points of a graph represent the states of a complex system (e.g. a particular phase of a molecular biological process), the conventional graph traversal algorithms, such as the algorithm A*, are not suitable for finding the best decision in a given moment. (The algorithm A* combines the optimality of simple horizontal graph traversal with the benefit of using heuristics to select the likely best decision in a particular case. As a result, only a small part of the generally extraordinarily large state graphs, in which the number of size of the graph is an exponential function of the number of the next possible steps in any given step, shall be visited since generally, no one is capable of travelling through such graphs.)

In the present case the conventional algorithms (e.g. algorithm A*) cannot be used because the parameters of the proposed excitation may also contain real numbers aside from discrete values, thus the number of possibilities available in a given moment is uncountably infinite, but even in the case of discretization, an extremely high branching factor should be taken into account, for which the common algorithms are not suitable at all as they are designed for optimality. However, if an optimal solution is not an absolute requirement, other algorithms could be used that result in a "fairly good" solution regarding the possibilities. In that case, even with a simulation using real numbers, a comparatively good result may be obtained even if those algorithms do not guarantee to find the best possible solution or the fastest possible solution. One of the algorithms based on such metaheuristics is, for example, the genetic algorithm and the simulated annealing, the latter optionally including multiple cooling cycles.

The above mentioned metaheuristics are basically methods by means of which the global minimum of a multidimensional continuous function can be determined. A common feature of these methods is that they are stochastic wherein to find the global minimum with full certainty requires infinite time, but they are able to find comparatively good solutions within a finite time period.

A genetic (evolutionary) algorithm imitates the process of natural evolution. In the course of performing the algorithm, in a first step, a population is created from a plurality of excitation sets in a predetermined way, for example randomly or by using another heuristic method, and then these populations are subject to competition with each other. The aim of the competition is to approach the target state so closely as possible, which is measured by the fitness value. This value is calculated in a manner that before running the algorithm, a time window for comparison is specified. Each step of the simulation within this time window will then be compared to the target state, and from these steps the one with the smallest difference between the target state and the state of the simulation in the particular step will be selected. The fitness value is defined as the difference between these two states, i.e. the sum of the squares of the differences between the state variables belonging to each network point (consequently, a lower fitness value means a better fit). The cost of individual excitations in an excitation set are then added to the fitness value, said excitation costs preferably being adjustable in advance. In case the cost of an excitation is low, the target state can be better approximated but using a larger number of individual excitations, while with a high cost a lower number of excitations (interventions) are provided but the result will likely be less precise.

After calculating the fitness values the excitation series with lower fitness values (i.e. excitation series generating simulation states better fitting to the target state) will survive to the next run of the competition (i.e. into the next generation) with greater likelihood.

The remaining individuals of the population will be determined for the next simulation step by using the excitations selected in the previous step in the following way. A new individual is created from two excitation series (parents) freely selected from the surviving excitation series by crossing over and, with a certain likelihood, by mutation.

At crossing over the new individual randomly receives one part of its excitations from one of its parents, and the other part of its excitations from its other parent.

Additionally, the excitation series of the new individual is modified with a predetermined likelihood (e.g. 5%) or with a preferably adjustable likelihood (this can also be referred to as a mutation), in course of which an excitation may be removed, or a new excitation may be added, or the parameters of an existing excitation may be modified.

The generated new population is again subject to competition, whereby the simulations are carried out and new fitness values are calculated. These steps are repeated until the minimum of the fitness value achieves a sufficiently low value or a predetermined number of simulations have been completed. In the following, an example on the application of a genetic algorithm in a network having 3 points will be described.

EXAMPLE 6

Initial state:
0
0
0
Target state:
0
3
1
Definition of the target point:
energyN 1:2 (let the target function be equal to the value of the state variable "energy" in step No. 2 or step No. 3)
Definition of the excitation function:
0:2 dirac 0:4 0:5 (for any node, an excitation of the type Dirac-delta with an amplitude between 0 and 5 could be tested between the time steps 1 and 5)

Initial population (initial group of excitations):
0 dirac 2 5, 1 dirac 3 2
1 dirac 3 1, 2 dirac 0 1
2 dirac 1 1, 2 dirac 2 0

From the above group of excitations the following three functors can be produced as a perturbation matrix:
energyNPF.cdat:

| | |
|---|---|
| 0 0 5 0 | -- functor of the first excitation |
| 0 0 0 2 | |
| 0 0 0 0 | |
| 0 0 0 0 | -- functor of the second excitation |
| 0 0 0 1 | |
| 1 0 0 0 | |
| 0 0 0 0 | -- functor of the third excitation |
| 0 0 0 0 | |
| 2 1 0 0 | |

If it is assumed that the simulation is a simple constant model in which every point keeps its given state, the first three steps of the simulation will result the following output matrixes:

| | |
|---|---|
| 0 0 5 5 | -- first simulation step |
| 0 0 0 2 | |
| 0 0 0 0 | |
| 0 0 0 0 | -- second simulation step |
| 0 0 0 1 | |
| 1 1 1 1 | |
| 0 0 0 0 | -- third simulation step |
| 0 0 0 0 | |
| 2 3 3 3 | |

From the above output matrices the following fitness values (F) can be calculated:

simulation No. 1, step No. 2 (the difference between column 2 of the output matrix No. 1 and the target state is calculated as the sum of the squares of the differences between each element):

$$F=(0-0)^2+(0-3)^2+(0-1)^2+2CP=12$$

where CP is the cost of adding a perturbation, which, in the current case, is 1, i.e. CP=1.

simulation No. 1, step No. 3 (the difference between column 3 of the output matrix No. 1 and the target state):

$$F=(5-0)^2+(0-3)^2+(0-1)^2+2CP=27$$

where the cost of perturbation is again CP=1.

From the above two results, the better one, namely the one with the smaller value is selected, therefore the fitness value of the first excitation is 12.

simulation No. 2 (the two steps are identical):

$$F=(0-0)^2+(0-3)^2+(1-1)^2+2=11$$

simulation No. 3:

$$F=(0-0)^2+(0-3)^2+(3-1)^2+2=15$$

Hence, if there are two surviving individuals for the next generation, they will be the excitations belonging to the simulations No. 1 and 2.

Subsequently, a missing child is then generated using the two parents so that again three excitations will participate in the next round of simulations:

In this case the parent excitations are as follows:
0 dirac 2 5, 1 dirac 3 2—first parent
1 dirac 3 1, 2 dirac 0 1—second parent After crossing over the parents, the following child excitation is obtained:

1 dirac 3 1, 1 dirac 3 2

When mutation also takes place, the following child excitation may be obtained, for example:

1 dirac 3 1, 1 dirac 2 2

The new population containing the mutated child excitation has therefore three elements again.

The time series (output matrix) of the new excitation is:

| 0 0 0 0 |
|---|
| 0 0 2 3 |
| 0 0 0 0 |

The fitness value for the second simulation step, like in the first step, is F=12 and for the third simulation step (where the second row of the perturbation matrix is 0 2 1):

$$F=(0-0)^2+(3-2)^2+(0-1)^2+2CP=4,$$

wherein CP=1.

The final fitness value is the smaller one of the results of the two simulation steps (steps No. 2 and 3), that is F=4.

Since this value is significantly better than the previous fitness values, this excitation will certainly be kept in the next generation.

A key feature of the algorithm of the simulated annealing is that a small movement is made on the search surface in every step. In the method according to the invention it means that a new excitation is added to the group of test excitations, or an excitation is removed from the group, or the parameters of an existing excitation are slightly modified. If the value of the function is smaller in a new position of the search space than in the previous position, the algorithm will enter the new position, so the new position will then be the initial position of further search. In the method of the invention, the value of the function corresponds to the difference between the system state resulting from the simulation and the desired target state, while the position of the search space corresponds to the series of the test excitations applied in the given simulation step. If the value of the function in the new position is higher than the current value, the new state will be discarded at a high likelihood, but at a predetermined (small) likelihood it is still accepted in order to avoid sticking in local minima. The exact value of the aforementioned likelihood is controlled by an external parameter "temperature". In case of a high temperature, the return to a previous position is allowed with a higher likelihood, while at a lower temperature, the likelihood of accepting a higher-energy position is also lower. The exact definition of acceptance is as follows:

$$P_{accept}=e^{(-F/T)},$$

where F is the difference between the new value and the pervious value (fitness), and T is the temperature. When the algorithm is executed, the temperature starts from a high value and is continuously decreased to zero. In case of a fast decrease schedule the run time is shorter but the result is of lower quality, while in case of a slow decrease, the computation takes a long time but the global optimum of the simulation (which is the minimum of the fitness value in the present case) can be approached very well. Warming/cooling cycles may alternately be repeated, too.

In the following, an example will be described on the application of the simulated annealing algorithm.

EXAMPLE 7

In case of simulated annealing, modification of a state corresponds to the mutation step and the calculation of energy corresponds to the calculation of the fitness when compared to the previously described genetic algorithm.

Let the target functions and the excitation definitions be the same as in Example 6.

The first excitation is:

1 dirac 3 2, 1 dirac 3 1, 2 dirac 1 1

Simulation:

| 0 0 0 0 |
|---|
| 0 0 0 3 |
| 0 1 1 1 |

After simulation the system's energy is:

$$E=12(3^2)+3$$

(The perfect solution is missed here because it comes too late as the search window is 1:2. Should the search window be 1:3, the fourth column (0 3 1) of the above excitation matrix would result in a perfect fit, but since step No. 4 is not within the search window, this column is disregarded.)

Neighbour state (mutation):

1 dirac 3 2, 1 dirac 1 1, 2 dirac 1 1

The result:

| 0 0 0 0 |
|---|
| 0 1 1 3 |
| 0 1 1 1 |

The system's energy after the new simulation is:

$$E=7(3-1)^2+3,$$

which is accepted.

Next state:

1 dirac 3 2, 2 dirac 1 1 (one excitation has been removed)

| 0 0 0 0 |
|---|
| 0 0 0 3 |
| 0 1 1 1 |

The system's energy:

$$E=(3-0)^2+2=11,$$

which is worse than the previous energy value.

Acceptance likelihood (T=0.01): $P_{accept}=\hat{}(-(11-7)/0.01)=\hat{}-400=10\hat{}174\sim0$.

Acceptance likelihood (T=1): $P_{accept}=\hat{}-4=0.02$

Acceptance likelihood (T=10): $P_{accept}=\hat{}-0.4=0.67$

In the above equations T represents the current value of the temperature parameter.

Enumeration of Steady States

In a preferred embodiment of the method according to the invention, each of the simulation rounds is run for a sufficiently long time so that the network reaches its steady state, provided that the network is capable of reaching a steady state at all. During the execution of a set of simulations, various techniques may be used to enumerate the steady states of the system, but it is common for all of the available techniques that a plurality of simulations is to be completed and the steady states are determined at the end of the whole simulation process. In the method of the invention, a state is deemed steady if the state variables of all of the network points remain within a given range of tolerance around their final values for a given time period, or if said state variables periodically change.

In a preferred embodiment of the method of the invention, the following algorithm is used for the recognition of a periodical change of the state variables:

a) By moving backwards along the axis of time, a time point is sought in which the value of the examined state variable is equal to the final value of that state variable, or even if it is different from that value, but still within a range of tolerance.

b) If no such a time point is found, a value "false" is provided as a return value (there is no periodical change).

c) If such a time point is found (it is called a secondary time point), then starting from that time point and also starting from the time point belonging to the final value, steps are made backwards along the axis of time and the two values of the respective state variable are compared in every step.

d) If during moving backwards along the axis of time from the final time point, the secondary time point is reached, then a cycle is successfully identified and the length of the cycle is provided as a return value (which is the time difference between the final time point and the secondary time point).

d) The mean value calculated from all of the steps within the cycle from the primary time point up to the secondary time point is returned as a steady state value.

f) If in any one of the steps, the difference between the value of the state variable belonging to the particular time point and the final value exceeds the tolerance, the time point, which has been previously found, is discarded and the search for an appropriate value matching the state variable for the final value is further continued.

g) If during moving backwards along the axis of time, a given examination time period is over, the return value will be again "false" (there is no periodicity).

The description of the initial and target states generally contains the description of all state variables of the system, but for a certain type of systems, like biological systems, such a detailed description is not available at all. To supply the missing status data one can use the observation that the complex systems (like the systems modeled by the network according to the invention) have so many constraints (such as the relations of the network in the present case) that they have a relatively low number of different steady states. If it is assumed that the complex system under examination is in the proximity of one of these steady states, the description of the missing state variables may be filled using the state variables of the steady state. Accordingly, when carrying out a preferred embodiment of the method according to the invention, an initial state functor is generated randomly (or according to the specified "learning" algorithms), the simulation is started and ran until the network has reached a steady state. This steady state is then inserted among the steady states that have already been determined before.

The steady states may be classified in the following way:

A steady state does not necessarily mean a state without movement. When the system steadily makes a periodical movement without any external intervention, it is also regarded as a steady state. This kind of steady state is called a limit cycle.

When more than one periodic movement is simultaneously present in the steady state of the system but their ratio is irrational, the whole system is still in a steady state, although a strictly periodical behavior cannot be identified and therefore the system is in a quasi-periodic state. This kind of state is called a limit torus.

The so called "strange attractor" is a special (recently recognized) class of the steady states. In the 1980's, it was discovered in the field of chaos theory that certain systems (e.g. the Lorenz-attractor) enter an aperiodic, non-self-repeating, bounded and unpredictable (save for a short-term prediction) path even without an external intervention (butterfly effect). Such a state can only be discovered in a multidimensional system, like the networks according to the invention (wherein each of the network points represents at least one dimension), through extended observation and by using sophisticated mathematical tools.

The above algorithm is capable of identifying the fixed points and the limit cycles, and it is also capable of finding certain limit tori (if only the system as a whole is in a limit torus but the network points themselves are in limit cycles), but may not be able to find other limit tori (when a network point itself is also in a limit torus). The aforementioned algorithm, however, is unable to find strange attractors.

In the method according to the invention, during the simulation the steady states of the network (or the points corresponding thereto in the state space, i.e. the so-called attractors) can be found, for example, by means of the following methods.

a) Searching for Attractors by Using a Clustering Algorithm

In this method a given number of simulations are executed and all of the steady states are stored. The steady states are then grouped by a clustering algorithm (e.g. XMeans, DBSCAN, OPTICS) and the center points of the groups are regarded as the found attractors. This method allows finding the center point of an attractor basin in the most precise manner, provided that the system has multiple very similar attractors.

b) Searching for Attractors in Real Time

When searching for attractors in real time, each of those steady states which differ from the previous attractors to an extent exceeding a given tolerance is indicated as a new attractor. A drawback of this method is that if there are multiple attractors in a given attractor basin, the attractor which has been first found will be provided as a result, instead of the true center points of the attractor basins. However, an advantage of this method is that not only random steps can be made, but a more directed search can be done using the existing initial and target states. For the search, the following options are available, for example:

i) trajectory-based search: the closer the initial state is to the steady state, the greater step is made away from the attractor.

ii) gradient-based search: until a new attractor is found, the step size is increased exponentially while moving from the preceding initial state in the direction of the gradient of the trajectory.

The method according to the invention is particularly suitable for use, for example, in designing targeted drugs, wherein the initial state may be a phenotype belonging to a given disease and the target state may be a healthy state, and wherein the result of the network simulation is the shortest chain of actions between the two states. The method according to the invention allows searching for new, even personalized targeted therapies, as well as finding multi-target drugs. Another field of application may be, for example, the examination of the behavior of the connectivity system within a social group, in which it may be established, for example, using dynamics from the field of game theory, that which members of a social group are mostly capable of enhancing the cooperation within the group.

In view of the above, the method according to the invention comprises the following main steps as illustrated by the flow diagram shown in FIG. 2.

The method according to the invention may be used for designing an intervention into the behavior of a real complex system by means of simulations, said system being modeled by a network in which the objects of the real system are represented by points, and the relations between the objects are represented by edges between the network points, and wherein the state of the objects are described by a set of parameters and the relations associated with the edges are described by time functions.

In the first step S200 of the method, the parameter values belonging to an initial state of the objects of the real system and the parameter values belonging to the desired target state are obtained. These data may be obtained either through measurements on the real objects of the particular system, for example by measuring technical, social or other features of the objects, or by reading said parameter values from one or more databases.

In the next step S210, the initial values and the desired target values of the parameters of the points in the network modeling the system are set. To this end, the real parameters of the system are mapped into parameters of the simulation model and, if necessary, the ranges of the values of the parameters may also be modified (e.g. limitation, extension, discretization, etc.) so that the simulation can be performed with the required efficiency but at a substantially higher speed.

In the next step S220, an initial set of test excitations is generated for at least one point of the network in a predetermined manner, for example randomly or by using another heuristic method. In case of complex networks, it is typical that the excitation of a number of points is necessary to sufficiently approach the desired target state. The test excitations are preferably described for the network in the form as detailed above.

In step S230, using the test excitations a simulation is executed to simulate the behavior of the network, i.e. the network is evolved into a set of following states using the given test set of excitations. If the network is not brought into a positive feedback state in response to the current test set of excitations (which may be avoided, for example, by applying an appropriate normalization function), then in step S240, the termination condition of the given simulation round is detected. In a given round, a simulation may also be run for a predetermined simulation time period, i.e. a simulation time window may be defined. Alternatively, the steady state of the network may be detected within a sufficiently long time window. The steady state may either be a point-like state or a periodically repeating state.

After detecting the termination condition, in step S250, the difference between the parameter values belonging to the desired target state and the parameter values resulting from the simulation is calculated and stored for each network point, and in step S260, using the difference between the parameter values and the number of the test excitations, another set of test excitations is generated. Generating the next set of test excitations may be carried out, for example, by means of a simulated annealing or a genetic algorithm as described above in detail, or depending on the nature of the complex systems, also by means of other metaheuristic algorithms, or in a specific case, even in entirely random fashion.

The steps S230 to S260 are then repeated (in step S270) until a predetermined termination condition becomes true when the whole simulation process is stopped. The entire process of repeated simulations is preferably terminated when the difference value decreases below a predetermined threshold or when the number of iterations reaches a predetermined value.

Finally, in step S280, from among the stored simulation results the simulation result which best fits to the desired target state is selected and the set of test excitations generating this result will be regarded as the set of excitations transferring the network from the initial state to the target state. Additionally, any steady states found during the simulation may also be stored. The thus obtained excitation set is then output to the user.

Alternatively, in this step multiple well-fitting sets of test excitations are also returned as a final result of the simulation.

In a preferred embodiment of the method according to the invention, in each iteration, the steady states (as termination conditions) possibly found in step S240 are stored, and at the end of the design process the list of the stored steady states and the number of simulations that were needed to reach the steady states are all provided for the user. When listing the steady states, every state within a certain predetermined tolerance range is regarded as the same state.

Now the configuration and the operation of an exemplary computer system 300 used for carrying out the simulations in the method according to the present invention will be described with reference to FIG. 3 which schematically illustrates the main functional elements of the system 300 along with their interrelations.

In the system 300 the networks to be simulated could generated by means of the module Netgen 302 on the basis of mathematical models of complex systems. The input of the module Netgen 302 is the definition of the type of the network to be generated, provided in a text format (e.g. smallworld), and additionally, any numeric parameters further defining the network to be generated (e.g. n=1000, k=3, p=0.1). The output of the module Netgen 302 is a data set which appropriately describes the network for the simulation program. The output of the module Netgen 302 is stored, for example, in a so-called CNET file.

Another data input module is the module Nconv 304, the input of which is the specification of a real complex network in a foreign format, and the output of which is again the CNET data file the simulator program can interpret.

A further data input module is the Dconv 306 that provides the functors of the simulation excitations specified for the network. The input of the module Dconv 306 is a matrix in a foreign file format, and the output of which is a functor the simulator program can interpret, said functor being stored, for example, in a CDAT file.

Finally, yet another data input module is the module Generate 308 that generates the output functors on the basis of a textual description, and wherein the output functors may also be stored in a CDAT data file.

The module Nedit 310 modifies the properties of the network (e.g. addition or removal of parameters, such as modification of edge weights). During its operation the module Nedit 310 modifies the CNET file used as input for the simulation.

The module Dedit 312 modifies the properties of the functors (e.g. size, storage mode, special flags, such as periodic flags) in a manner that it modifies the content of the CDAT file serving as input for the simulation.

The module Normalize 314 primarily modifies the parameter values of the network in order to fulfill certain requirements of the simulation (particularly those of the given simulation model). For example, it may remove, the self-links and double edges. The module Normalize 314 modifies the CNET data file used as input for the simulation.

The module Model 316 is, for example, a DLL file, the function PerStep of which is called by the simulator in each step. The task of the module Model 316 is to calculate how the state variables change step by step during the simulation. Practically, this module contains the system equations in an algorithmic form.

The module Simulate 318 functions to calculate the time-dependent evolution of the network based on the simulation model. Its input is a CNET file describing the network to be simulated and a CDAT data file describing the initial values and the possible perturbations. The module Simulate 318 reads a corresponding CDAT data file for each state variable. The output of the module includes a functor (CDAT data file) for each state variable containing the time series of the given state variable and, if the network has been changed during the simulation, also the description of the modified network (CNET data file). Additionally, it is preferred that the module Simulate 318 also carries out a search for any steady states of the network, which may be needed to stop the simulation, but knowledge of the steady states in itself may also provide useful information for designing further interventions, for example.

The module Calculate 320 functions to calculate various measurement values from the simulation time series. Its input is a CDAT data file containing the time series of the simulation and its output is the given measurement value, preferably in a text format.

The module Turbine viewer 322 is a separate program module that is capable of graphically displaying both the networks and the data.

The module Designer 324 includes the metaheuristics, i.e. the simulated annealing or the genetic algorithm. For example, when the excitation sets are generated by a genetic algorithm, this module determines the next excitation population to be tested from the previous excitation populations and their fitness values, all having received as an input.

The module Fitness 326 calculates a fitness value for a certain excitation set from the simulation results. Its input includes the time series of the simulation and the target state (with its definition).

The module Design 328 constitutes a simulation framework that iteratively runs the simulator and calls the functions of the module Designer 324 and the module Fitness 326 at the beginning and at the end of the simulation rounds.

In the above described system 300, only the data files describing the network are preferably stored in the memory of the computer, and any other data required for the simulation are stored separately on a data carrier, to/from which data can be directly written/read during the simulation, thus much larger networks than ever before may be analyzed in this way. The speed of the simulation may be further increased by "smoothing" the network in the memory by means of a special internal algorithm, i.e. the physical storage locations of the network points interconnected by edges are as close to each other as possible, thus the memory access rate of the graphics card, which is usually a critical feature, may be further increased.

The above simulation system 300 may be completed with a multi-purpose distribution algorithm, by means of which several subsequent simulations can be allocated in a highly scalable manner, for example, to one or more processors within one computer, to each of the computers of a super computer system, or to a grid including a plurality of computers, for example by using a framework such as BOINC or TORQUE. These all allow fast and repeated simulations of large networks, thus beyond the aforementioned methods, the simulation system may also be used as a search function of other artificial intelligence algorithms.

In another aspect of the invention a processor device is provided for carrying out the method according to the invention. The main components of the device and their connectivity arrangement are illustrated in FIG. 4.

As shown in FIG. 4, the device according to the invention is a processor device 400, preferably a computer, configured to design interventions into the behavior of complex systems. The complex system is modeled by a network in which the objects of the system are represented by network points and the relations between the objects are represented by edges between the network points, and wherein the states of the objects are described by a parameter set and the interactions associated with the edges are described by functions of time. The device 400 comprises a data carrier 402 adapted for storing the network structure, the parameter values of the network points, the functions of interactions associated with the network edges, and the computer program modeling the behavior of the network. The device 400 further comprises a memory unit 404 and a processor-based central processing unit 406 electronically coupled to both the aforementioned data carrier 402 and the memory unit 404. The central processing unit comprises a data input unit 408, a metaheuristics unit 410 for generating a test set of excitations, a simulation module 412 and a comparison module 414 for comparing the target state of the simulation with the target state or the steady state of the simulation. More particularly, the method according to the invention is carried out by an intervention design unit 416 comprising the metaheuristics unit 410, the simulation module 412 and the comparison module 414. The data input unit 408 may include, for example, the functions of the data input modules 302, 304, 306, 308 shown in FIG. 3. The metaheuristics unit 410 may include, for example, the functions of the module Designer 324 shown in FIG. 3. The simulation module 412 may include, for example, the functions of the module Simulate 318 shown in FIG. 3. The comparison module 414 may include, for example, the functions of the module Fitness 326 shown in FIG. 3.

In a third aspect of the invention, the present invention also relates to a computer program product comprising computer readable instructions which, when run on a processor device, such as a computer, cause the processor device to carry out the method according to the invention. The above mentioned computer program product may be stored, for example, on the data carrier 402 of the above processor device 400 or it can be loaded into the memory unit 404 thereof.

A beneficial application of the invention design in a network of interactions between proteins is illustrated in FIG. 5. The network used in this example, which was published in 2011, constitutes the signal transmission network of a leukemic leukocyte (cytotoxic T-cell). Normally, after prolonged activation such a cell should kill itself so that harmful autoimmune processes could be avoided. This state is shown on the right side of FIG. 5. With a special type of leukemia (LGL), however, the above process does not take place but instead, a continuously proliferating cell form remains alive after activation, as shown on the right side of FIG. 5. The presence of cells in such a state significantly damages the most types of tissue, including the correctly operating leukocytes as well, thereby causing the symptoms of leukemia. The aim of the intervention to be designed is to change the state of the diseased cells, shown on the left side of FIG. 5, to a healthy state, shown on the right side of the figure. The accepted ways of interventions include either the activation or the inhibition of the proteins in the network, with the restriction that only those forms of intervention are allowed where a corresponding treatment is available according to the database DrugBank dated Dec. 11, 2013. For designing the intervention the genetic algorithm-based search engine was used. The parameter space of the search was defined as follows:

statusN+tlgl-druggable-ids.txt#ID dirac −1(ID=+tlgl-inhibitable-ids.txt); 1(ID=+tlgl-activatable-ids.txt) 0:1:10 i.e. excitations of the type Dirac-delta with integer time steps ranging from 0 to 10 for the identifiers of proteins that can be treated with drugs, by applying an amplitude of 1 in case of an activatory drug and −1 in case of an inhibitory drug, according to the mode of action of the corresponding drug.

After running the program, the following list of excitations was obtained:

22 dirac −1 2.000000
4 dirac −1 0.000000 which corresponds to the inhibition of PDGFR (ID 4, step No. 0 (first step)) and the inhibition (−1) of NF-κB (ID 22, step No. 2, (third step)). According to the data base DrugBank, the applicable drugs are for example Sunitinib or Pazopanib for PDGFR, and for example Triflusal, Thalidomide or Pranlukast for NF-κB.

Since only those interventions were selected that correspond to targets of clinically validated medicines, the efficacy of each of the separate interventions is well supported. However, it is to be noted that the obtained intervention sets should not be applied without a clinical validation of the joint effect of the interventions because of the possible error of modeling and possible non-described interactions of the used drugs.

The invention claimed is:

1. A computer-implemented method for designing intervention into the behavior of a real complex system of biochemical nature, the method comprising:
    a) modeling the real complex system by a network of objects and relations between said objects, wherein said objects of the system are represented by network points and relations are represented by edges between the network points, and wherein the states of the objects are described by a parameter set and the relations associated with the edges are described by functions of time;
    b) for each object of the real system, obtaining values for each parameter of said parameter set both for an initial state and a desired target state thereof;
    c) setting the initial values and the desired target values of the parameters of the network points;
    d) using a predetermined metaheuristic algorithm, automatically generating an initial set of test excitations for at least one point of the network, the initial set of test excitations including a predetermined number of test excitations defined by the metaheuristic algorithm;
    e) simulating the behavior of the network by using the set of test excitations;
    f) detecting whether a simulation termination condition in a given simulation step is true and if so, stopping the simulation;
    g) after stopping the simulation, calculating and storing, for each network point, the difference between the parameter values belonging to the desired target state and the parameter values produced by the simulation;
    h) automatically generating a next set of test excitations by using the predetermined metaheuristic algorithm, the next set of test excitations being generated to more closely approach the target state based on the previous test excitations having the smallest difference between the parameter values belonging to the desired target state and the parameter values produced by the simulation, and the number of text excitations in the next set being defined by the metaheuristic algorithm;
    i) iteratively repeating steps e)-h) to reduce the difference between the parameter values produced by the simulations and the parameter values of the target state until a predetermined entire termination condition is satisfied;
    j) from among the stored simulation results, selecting the simulation result best matching the desired target state, the test set of excitations which produced said best matching simulation result is regarded as a final excitation set transferring the network from its initial state to its target state; and
    k) outputting the final excitation set as the intervention into the behavior of the real complex system of biochemical nature.

2. The method according to claim 1, wherein the initial values and the desired target values of the parameters of the objects are determined by measurements on the objects.

3. The method according to claim 1, wherein the initial values and the desired target values of the parameters of the objects are read from a database.

4. The method according to claim 1, wherein a simulation time window is defined in advance and the simulation termination condition is regarded satisfied if within a sufficiently long time window, a steady state of the network is detected.

5. The method according to claim 4, wherein the resulting steady states are stored, and wherein the method further comprises outputting a list of the stored steady states and the number of simulations reaching each steady state.

6. The method according to claim 5, wherein all of the states within a specific tolerance range are regarded as the same state.

7. The method according to claim 1, wherein the predetermined entire termination condition comprises obtaining a difference value between the parameter values belonging to the desired target state and the parameter values produced by the simulation that is below a predetermined threshold.

8. The method according to claim 1, wherein the predetermined entire termination condition comprises reaching a predetermined number of simulation iterations.

9. The method according to claim 1, wherein the metaheuristic algorithm is a genetic algorithm, the number of test excitations is more than one per simulation, a fitness value for each simulated set of test excitations is calculated by the difference between the parameter values belonging to the desired target state and the parameter values produced by the simulation, and the next set of test excitations is generated from the sets of test excitations having the best fitness values by crossing over and/or mutation.

10. The method according to claim 1, wherein the metaheuristic algorithm is a simulated annealing algorithm, the number of test excitations is one per simulation, and an energy value for each simulation iteration is calculated by the difference between the parameter values belonging to the desired target state and the parameter values produced by the simulation.

11. The method according to claim 1, wherein the intervention is a targeted drug, the real complex system of biochemical nature is a cell, the initial state is a phenotype belonging to a particular disease, the target state is a healthy state, and the final excitation set comprises the shortest chain of actions between the initial state and the target state.

12. A processor device for designing intervention into the behavior of a real complex system of biochemical nature, the device comprising:

a data carrier storing a model of a real complex system of a biochemical nature, the model comprising a network of objects represented by network points and relations between the objects being represented by edges between the network points, wherein the states of the objects are described by a parameter set and the relations associated with the edges are described by functions of time;

a processor device; and a memory device encoding instructions that, when run on the processor device, cause the processor device to:
 (a) obtain values for an initial state and a desired target state for each parameter of the parameter set for each object;
 (b) set the initial values and the desired target values of the parameters of the network points;
 (c) automatically generate an initial set of test excitations for at least one point of the network, the initial set of test excitations having a number of test excitations selected using a predetermined metaheuristic algorithm;
 (d) simulate behavior of the network using the set of test excitations;
 (e) stop the simulation when a simulation termination condition in a given simulation step is detected;
 (f) after the simulation is stopped, calculate and store the differences between the parameter values belonging to the desired target state and the parameter values produced by the simulation for each network point;
 (g) automatically generate a next set of test excitations selected to more closely approach the target state based on the previous test excitations having the smallest differences by using the predetermined metaheuristic algorithm;
 (h) iteratively repeating steps (d)-(g) until a predetermined termination condition is satisfied;
 (i) from among the stored simulation results, selecting the simulation result best matching the desired target state, the test set of excitations which produced said best matching simulation result is regarded as a final excitation set transferring the network from its initial state to its target state; and
 (j) outputting the final excitation set as the intervention into the behavior of the real complex system of biochemical nature.

13. The processor device of claim 12, wherein the intervention is a targeted drug, the real complex system of biochemical nature is a cell, the initial state is a phenotype belonging to a particular disease, and the target state is a healthy state.

14. A non-transitory computer program product comprising computer readable instructions which, when run on a computer, cause the computer to:
 a) model a biochemical system with a network of objects represented by networks points and relations between the objects represented by edges between the network points, wherein the states of the objects are described by a parameter set and the relations associated with the edges are described by functions of time;
 b) for each object of the biochemical system, obtain values for each parameter of the parameter set for an initial state and a desired target state thereof;
 c) set the initial values and the desired target values of the parameters of the network points;
 d) automatically generate an initial set of test excitations for at least one point of the network using a predetermined metaheuristic algorithm, the initial set of test excitations including a predetermined number of test excitations defined by the metaheuristic algorithm;
 e) simulating the behavior of the network using the set of test excitations;
 f) detect whether a simulation termination condition in a given stimulation step is true and if so, stop the simulation;
 g) after the simulation is stopped, calculate and store, for each network point, the difference between the parameter values belonging to the desired target state and the parameter values produced by the simulation;
 h) based on the differences and number of test excitations, automatically generate a next set of test excitations using the predetermined metaheuristic algorithm, the next set of test excitations being generated to more closely approach the target state based on the previous test excitations having the smallest difference between the parameter values belonging to the desired target state and the parameter values produced by the simulation, and the number of text excitations in the next set being defined by the metaheuristic algorithm;
 i) iteratively repeat steps e)-h) to reduce the difference between the parameter values produced by the simulations and the parameter values of the target state until a predetermined termination condition is satisfied;
 j) from among the stored simulation results, select the simulation result best matching the desired target state, where the test set of excitations which produced the best matching simulation results is regarded as a final excitation set transferring the network from its initial state to its target state; and
 k) outputting the final excitation set as a designed intervention into the biochemical system.

15. The computer program product of claim 14, wherein the biochemical system is a cell, the initial state corresponds to a phenotype of a given cell type, and the target state is either a healthy or an apoptotic state.

16. The method according to claim 14, wherein the metaheuristic algorithm is a genetic algorithm and a fitness value for each simulation iteration is calculated by the difference between the parameter values belonging to the desired target state and the parameter values produced by the simulation.

17. The method according to claim 14, wherein the metaheuristic algorithm is a simulated annealing algorithm and an energy value for each simulation iteration is calculated by the difference between the parameter values belonging to the desired target state and the parameter values produced by the simulation.

* * * * *